US005691153A

United States Patent [19]

Recker et al.

[11] Patent Number: 5,691,153
[45] Date of Patent: Nov. 25, 1997

[54] GENETIC MARKERS TO DETECT HIGH BONE MASS

[75] Inventors: Robert R. Recker; Mark L. Johnson; Donald B. Kimmel; Guodong Gong; Susan M. Recker, all of Omaha, Nebr.

[73] Assignee: Creighton University, Omaha, Nebr.

[21] Appl. No.: 708,175

[22] Filed: Sep. 6, 1996

[51] Int. Cl.$^6$ .................................................. C12Q 1/68
[52] U.S. Cl. .................................... 435/6; 435/91.2
[58] Field of Search ............................... 435/6, 91.2

[56] References Cited

U.S. PATENT DOCUMENTS

| | | | |
|---|---|---|---|
| 4,710,382 | 12/1987 | Recker | 514/12 |
| 4,870,054 | 9/1989 | Recker | 514/12 |
| 5,532,226 | 7/1996 | Demarest et al. | 514/134 |
| 5,545,534 | 8/1996 | Akita et al. | 435/7.92 |
| 5,547,685 | 8/1996 | Cullinan | 424/600 |
| 5,550,138 | 8/1996 | Sohda et al. | 514/361 |
| 5,593,833 | 1/1997 | Morrison et al. | 435/6 |

OTHER PUBLICATIONS

Marcus, *J. Clin. Endocrinol. Metab.*, 81(1):1–5 (1996).
*Med. Lett. Drugs Ther.*, 38(965):1–3 (1996).
Lane et al., *J. Bone Joint Surg. Am.*, 78(4):618–632 (1996).
Recker, *J. Clin. Endocrinol. Metab.*, 76(1):14–16 (1993).

Gong et al., *Am. J. Hum. Genet.*, 59(1):146–151 (1996).

Kelly, *Br. J. Obstet. Gynaecol.*, 103 Suppl 13:20–27 (1996).

Arnaud, *Geriatrics*, 51(4):24–30 (1996).

Raab–Cullen et al., *Calcif Tissue Int*, 55(6):473–478 (1994).

Ross, *Arch Intern Med*, 156(13):1399–1411 (1996).

*Primary Examiner*—James Ketter
*Attorney, Agent, or Firm*—Jaeckle Fleischmann & Mugel, LLP

[57] ABSTRACT

The invention provides the chromosome location of an autosomal dominant gene associated with high bone mass. As a result of this localization, the presence of a polymorphism linked to the autosomal dominant gene in a subject can be detected by analyzing human chromosome 11 of the subject for the presence of the polymorphism located about 30 cM around D11S987 and linked to the autosomal dominant gene. The analysis of chromosome 11 can be accomplished by amplifying the polymorphism, separating the amplified polymorphism to generate a polymorphism pattern, and correlating the presence or absence of the polymorphism with the respective presence or absence of the autosomal dominant gene associated with high bone mass.

10 Claims, 2 Drawing Sheets

GENETIC MARKERS TO DETECT HIGH BONE MASS

FIELD OF INVENTION

The subject invention is directed to genetic testing, and more particularly to a method of detecting the presence of an autosomal dominant gene associated with high bone mass and also to identification of the location of the autosomal dominant gene in the human genome.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Two of the most common types of osteoporosis are Postmenopausal and senile osteoporosis.

Postmenopausal Osteoporosis

The most common type of osteoporosis is that associated with menopause. Most women lose between 20–60% of the bone mass in the trabecular compartment of the bone within 3–6 years after the cessation of menses. This rapid loss is generally associated with an increase of bone resorption and formation. However, the resorptive cycle is more dominant and the result is a net loss of bone mass.

Osteoporosis is a common and serious disease among postmenopausal women. There are an estimated 25 million women in the United States alone who are afflicted with this disease. The results of osteoporosis are both personally harmful, and also account for a large economic loss due to its chronicity and the need for extensive and long-term support (hospitalization and nursing home care) from the disease sequelae. This is especially true in more elderly patients. Additionally, osteoporosis is generally not thought of as a life threatening condition, but a 20–30% mortality rate is related with hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy bone and is particularly concentrated near the ends of the bone near the joints and in the vertebrae of the spine. The trabecular tissue is characterized by small structures which inter-connect with each other as well as the more solid and dense cortical tissue which makes up the outer surface and central shaft of the bone. This criss-cross network of trabeculae gives lateral support to the outer cortical structure and is critical to the biomechanical strength of the overall structure. In postmenopausal osteoporosis, it is, primarily, the net resorption and loss of the trabeculae which leads to the failure and fracture of the bone. In light of the loss of the trabeculae in postmenopausal women, it is not surprising that the most common fractures are those associated with bones which are highly dependent on trabecular support, e.g., the vertebrae, the neck of the femur, and the forearm. Indeed, hip fracture, Colle's fractures, and vertebral crush fractures are indicative of postmenopausal osteoporosis.

One of the earliest generally accepted methods for treatment for postmenopausal osteoporosis was estrogen replacement therapy. Although this therapy frequently is successful, patient compliance is low, primarily due to the undesirable side-effects of estrogen treatment. Frequently cited side-effects of estrogen replacement therapy include reinitiation of menses, bloating, depression, and fear of breast or uterine cancer. In order to limit the known threat of uterine cancer in those women who have not undergone a hysterectomy, a protocol of estrogen and progestin cyclic therapy is often employed. This protocol is similar to that which is used in birth control regimens, and often is not tolerated by many women because of the side-effects characteristic of progestin.

More recently, certain antiestrogens, originally developed for the treatment of breast cancer, have been shown in experimental models of postmenopausal osteoporosis to be efficacious. Among these agents is raloxifene (See, e.g., U.S. Pat. No. 5,393,763, and Black et al. 1994). In addition, tamoxifene, a widely used clinical agent for the treatment of breast cancer, has been shown to increase bone mineral density in post menopausal women suffering from breast cancer (Love et al. 1992).

Another therapy for the treatment of postmenopausal osteoporosis is the use of calcitonin. Calcitonin is a naturally occurring peptide which inhibits bone resorption and has been approved for this use in many countries (See, e.g., Overgaard et al. 1992). The use of calcitonin has been somewhat limited. Its effects are very modest in increasing bone mineral density and the treatment is very expensive.

Another therapy for the treatment of postmenopausal osteoporosis is the use of bis-phosphonates. These compounds were originally developed for use in Paget's disease and malignant hypercalcemia. They have been shown to inhibit bone resorption. Alendronate, one compound of this class, has been approved for the treatment of postmenopausal osteoporosis. These agents may be helpful in the treatment of osteoporosis, but these agents also have potential liabilities which include osteomalacia, extremely long half-life in bone (greater than 2 years), and possible "frozen bone syndrome" (e.g., the cessation of normal bone remodeling).

Senile Osteoporosis

Senile osteoporosis is similar to postmenopausal osteoporosis in that it is marked by the loss of bone mineral density and resulting increase in fracture rate, morbidity, and associated mortality. Generally, it occurs in later life, 70+ years. Although, in the past, it has been more common in females, with the advent of a more elderly male population, this disease is becoming a major factor in the health of both sexes. It is not clear what, if any, the role of hormones such as testosterone or estrogen have in this disease, and its etiology remains obscure.

Treatment of this disease has not been very satisfactory. Hormone therapy, estrogen in women and testosterone in men, has shown equivocal results; calcitonin and bis-phosphonates may be of some utility.

The peak mass of the skeleton at maturity is largely under genetic control. Twin studies have shown that the variance in bone mass between adult monozygotic twins is smaller than between dizygotic twins (Slemenda et al. 1991; Young et al. 1995; Pocock et al. 1987; Kelly et al. 1993), and it has been estimated that up to 60% of the variance in skeletal mass is inherited (Krall and Dawson-Hughes 1993). Peak skeletal mass is the most powerful determinant of bone mass in elderly years (Hui et al. 1989), even though the rate of age-related bone loss in adult and later life is also a strong determinant (Hui et al. 1995). Since bone mass is the principal measurable determinant of fracture risk, the inherited peak skeletal mass achieved at maturity is an important determinant of an individual's risk of fracture late in life. Thus, study of the genetic basis of bone mass is of considerable interest in the etiology of fractures due to osteoporosis.

Recently a strong interest in the genetic control of peak bone mass has developed in the field of osteoporosis. The interest has focused mainly on candidate genes with suitable polymorphisms to test for association with variation in bone mass within the normal range, or has focused on examination of genes and gene loci associated with low bone mass in the range found in patients with osteoporosis. The vitamin D receptor locus (VDR) (Morrison et al. 1994), PTH gene (Howard et al. 1995; Johnson et al. 1995; Gong et al. 1995) and the estrogen receptor gene (Hosoi et al. 1995; Morrison et al. 1995) have figured most prominently in this work. These studies are difficult because bone mass (the phenotype) is a continuous, quantitative, polygeneic trait, and is confounded by environmental factors such as nutrition, comorbid disease, age, physical activity, and other factors. Also, this type of study design requires large numbers of subjects. In particular, the results of VDR studies to date have been confusing and contradictory (Garnero et al. 1995; Eisman et al. 1995; Peacock 1995). Furthermore, the work thus far has not shed much light on the mechanism(s) whereby the genetic influences might exert their effect on bone mass.

While it is well known that peak bone mass is largely determined by genetic rather than environmental factors, studies to determine the gene loci (and ultimately the genes) linked to variation in bone mass are difficult and expensive. Study designs which utilize the power of linkage analysis (e.g. sib-pair or extended family) are generally more informative than simple association studies, although the later do have value. However, genetic linkage studies involving bone mass are hampered by two major problems. The first problem is the phenotype. Bone mass is a continuous, quantitative trait, and establishing a discrete phenotype is difficult. Each site for measurement may have several genes, many of which may be different from site to site. The second problem is the age component of the phenotype. By the time an individual can be identified as having low bone mass, there is a high probability that their parents or other members of prior generations will be deceased and therefore unavailable for study, and younger generations may not have even reached peak bone mass, making their phenotyping uncertain (for genetic analysis).

Regardless, linkage analysis can be used to find the location of a gene causing a hereditary "disorder" and does not require any knowledge of the biochemical nature of the disorder (i.e. a mutated protein that is believed to cause the disorder does not need to be known). Traditional approaches depend on assumptions concerning the disease process that might implicate a known protein as a candidate to be evaluated. The genetic localization approach using linkage analysis can be used to first find the general chromosomal region in which the defective gene is located and then to gradually reduce the size of the region in order to determine the location of the specific mutated gene as precisely as possible. After the gene itself is discovered within the candidate region, the messenger RNA and the protein are identified and, along with the DNA, are checked for mutations.

This latter approach has practical implications since the location of the disease can be used for prenatal diagnosis even before the altered gene that causes the disease is found. Linkage analysis can enable families, even many of those that do not have a sick child, to know whether they are carriers of a disease gene and to evaluate the condition of an unborn child through molecular diagnosis.

The transmission of a disease within families, then, can be used to find the defective gene. As used herein, reference to "high bone mass" is analogous to reference to a disease state, although from a practical standpoint high bone mass can actually help a subject avoid the disease known as osteoporosis.

Linkage analysis is possible because of the nature of inheritance of chromosomes from parents to offspring. During meiosis the two homologues pair to guide their proper separation to daughter cells. While they are lined up and paired, the two homologues exchange pieces of the chromosomes, in an event called "crossing over" or "recombination". The resulting chromosomes are chimeric, that is, they contain parts that originate from both parental homologues. The closer together two sequences are on the chromosome, the less likely that a recombination event will occur between them, and the more closely linked they are. In a linkage analysis experiment, two positions on the chromosomes are followed from one generation to the next to determine the frequency of recombination between them. In a study of an inherited disease, one of the chromosomal positions is marked by the disease gene or its normal counterpart, i.e. the inheritance of the chromosomal region can be determined by examining whether the individual displays symptoms of the disorder or not. The other position is marked by a DNA sequence that shows natural variation in the population such that the two homologues can be distinguished based on the copy of the "marker" sequence that they possess. In every family, the inheritance of the genetic marker sequence is compared to the inheritance of the disease state. If, within a family carrying an autosomal dominant disorder such as high bone mass, every affected individual carries the same form of the marker and all the unaffected individuals carry at least one different form of the marker, there is a great probability that the disease gene and the marker are located close to each other. In this way, chromosomes may be systematically checked with known markers and compared to the disease state. The data obtained from the different families is combined, and analyzed together by a computer using statistical methods. The result is information indicating the probability of linkage between the genetic marker and the disease allowing different distances between them. A positive result can mean that the disease is very close to the marker, while a negative result indicates that it is far away on that chromosome, or on an entirely different chromosome.

Linkage analysis is performed by typing all members of the affected family at a given marker locus and evaluating the co-inheritance of a particular disease state with the marker probe, thereby determining how often the two of them are coinherited. The recombination frequency can be used as a measure of the genetic distance between two gene loci. A recombination frequency of 1% is equivalent to 1 map unit, or 1 centiMorgan (cM), which is roughly equivalent to 1,000 kb of DNA. This relationship holds up to frequencies of about 20% (or 20 cM).

The entire human genome is 3,300 cM long. In order to find an unknown disease gene with 5-10 cM of a marker locus, the whole human genome can be searched with 165-330 informative marker loci spaced at 5-10 cM intervals (Botstein et al. 1980). The reliability of linkage results is established by using a number of statistical methods.

The method most commonly used for the analysis of linkage in humans is the LOD score method (Morton 1984; Morton et al. 1986) which was incorporated into the computer program LIPED by Ott (1976). Lod scores are the logarithm of the ratio of the likelihood that two loci are linked at a given distance to that they are not linked (>50 cM apart). The advantage of using logarithmic values is that they can be summed among families with the same disease. This becomes necessary given the relatively small size of human families.

By convention, a total lod score greater than +3.0 (that is, odds of linkage at the specified recombination frequency being 1000 times greater than odds of no linkage) is considered to be significant evidence for linkage at that particular recombination frequency; a total lod score of less than −2.0 (that is, odds of no linkage being 100 times greater than odds of linkage at the specified frequency) is considered to be strong evidence that the two loci under consideration are not linked at that particular recombination frequency.

Until recently, most linkage analyses have been performed on the basis of twopoint data; that is, the relationship between the disorder under consideration and a particular genetic marker. However, as a result of the rapid advances in mapping the human genome over the last few years, and concomitant improvements in computer methodology, it has become feasible to carry out linkage analyses using multipoint data; that is, a simultaneous analysis of linkage between the disease and several linked genetic markers, when the recombination distance among the markers is known.

Multipoint analysis is advantageous for two reasons. First, the informativeness of the pedigree is usually increased. Each pedigree has a certain amount of potential information, dependent on the number of parents heterozygous for the marker loci and the number of affected individuals in the family. However, few markers are sufficiently polymorphic as to be informative in all those individuals. If multiple markers are considered simultaneously, then the probability of an individual being heterozygous for at least one of the markers is greatly increased. Second, an indication of the position of the disease gene among the markers may be determined. This allows identification of flanking markers, and thus eventually allows isolation of a small region in which the disease gene resides. Lathrop et al. (1984) have written the most widely used computer package, LINKAGE, for multipoint analysis.

With an understanding of linkage analysis, the next concept behind the subject invention is that specific DNA sequences in an individual can undergo many different changes, such as deletion of a sequence of DNA, insertion of a sequence that was duplicated, inversion of a sequence, or conversion of a single nucleotide to another. Changes in a specific DNA sequence may be traced by using restriction enzymes that recognize specific DNA sequences of 4–6 nucleotides. Restriction enzymes cut (digest) the DNA at their specific recognized sequence, resulting in one million or so pieces. When a difference exists that changes a sequence recognized by a restriction enzyme to one not recognized, the piece of DNA produced by cutting the region will be of a different size. The various possible fragment sizes from a given region therefore depend on the precise sequence of DNA in the region. Variation in the fragments produced is termed "restriction fragment length polymorphism" (RFLP). The different sized-fragments reflecting different variant DNA sequences can be visualized by separating the digested DNA according to its size on an agarose gel and visualizing the individual fragments by annealing to a radioactively labeled DNA "probe". Each individual can carry two different forms of the specific sequence. When the two homologues carry the same form of the polymorphism, one band will be seen. More than two forms of a polymorphism may exist for a specific DNA marker in the population, but in one family just four forms are possible; two from each parent. Each child inherits one form of the polymorphism from each parent. Thus, the origin of each chromosome region can be traced (maternal or paternal origin).

Consequently, the present invention comprises genetic linkage analysis to identify an individual having the autosomal dominant gene associated with high bone mass. In addition, discovery of markers linked to the autosomal dominant gene will enable researchers to focus future analysis on a small chromosome region and will accelerate the sequencing of the autosomal dominant gene.

It is an object of the present invention to locate markers linked to the autosomal dominant gene associated with high bone mass and to identify the location of the autosomal dominant gene in the human genome.

It is a further object of the present invention to provide a genetic test specific for the autosomal dominant gene.

SUMMARY OF THE INVENTION

The present invention describes, for the first time, the chromosomal location which carries the gene responsible for high bone mass and provides a method of detecting the presence of a polymorphism linked to an autosomal dominant gene associated with high bone mass in a subject. The location of the autosomal dominant gene is on the long arm of human chromosome 11 (the q arm), more specifically about 30 cM around D11S987. A most probable location of the autosomal dominant gene is between D11S905 and D11S937, inclusive.

Linkage analysis with markers located on the long arm of human chromosome 11 is used to identify the inheritance of the allele causing high bone mass with 95% accuracy at this time. In particular, the test is carried out by studying the heritability of a combination of two or more polymorphisms linked to high bone mass among any number of suitable family members so as to allow the determination of the high bone mass phenotype. The test can be used to screen a subject for the presence/lack of the autosomal dominant gene associated with high bone mass. Presence of the gene, resulting in high bone mass, will protect a subject from osteoporosis.. Lack of the gene, and therefore lack of high bone mass, suggests that the subject may have a normal risk for osteoporosis.

The invention is based on the discovery of a kindred in which members inherit an autosomal dominant gene that results in extremely high bone mass. The gene responsible for this trait has been designated the Hbm gene. To date, 192 members of the kindred have been identified. Twenty-two of the members have been phenotyped for spinal bone mineral density (BMD) using DXA. A clear bimodal distribution of phenotypes was observed in this kindred. Affected members have a mean age and sex adjusted z-score for spinal BMD of 5.22±1.48 S.D. (range 3.81–7.80). Unaffected members have a mean z-score for spinal BMD of 0.44±0.92 S.D. (range 1.07–2.09). There are no other distinguishing clinical differences between affected and unaffected members of this family. A whole genome search strategy was used with ABI PRISM™ Mapping Panels to identify linked markers. Linkage analysis was performed using both two-point and multipoint analysis with the program LINKAGE. Initially, a model of autosomal dominance trait with full penetrance was used to find linked markers. A maximal LOD score of 4.055 was obtained in the region of marker D11S987 on chromosome 11. Haplotyping in this region indicated that one individual carried the haplotype but was scored as unaffected. This person's spinal BMD was the highest of the unaffected group. A model using an autosomal dominant trait with partial penetrance (0.9) was then used, and the LOD score for D11S987 increased to 4.474. Since bone density is a continuous, quantitative trait, a model using a quantitative trait analysis was also used. The LOD score for D11S987 increased to 5.207. Multipoint analysis was performed using the quantitative trait model and the maximum LOD score obtained was 5.726. The 95% confidence interval is bounded by markers D11S905 and D11S937 which places the Hbm gene in 11q12-13. Haplotype analysis places the Hbm locus within the same interval. No evidence for linkage was found in any other region of the genome using any of the three models. Several genes have been mapped to this region, however, none of these represent strong choices as a suspected identity for the Hbm gene. The discovery of the Hbm gene should have a dramatic impact on the understanding of the regulation of bone density and provide valuable new insights into the pathogenesis of diseases such as osteoporosis.

BRIEF DESCRIPTION OF THE FIGURES

These and other features and advantages of this invention will be evident from the following detailed description of preferred embodiments when read in conjunction with the accompanying drawings in which.

DETAILED DESCRIPTION OF THE INVENTION

Figure 1:
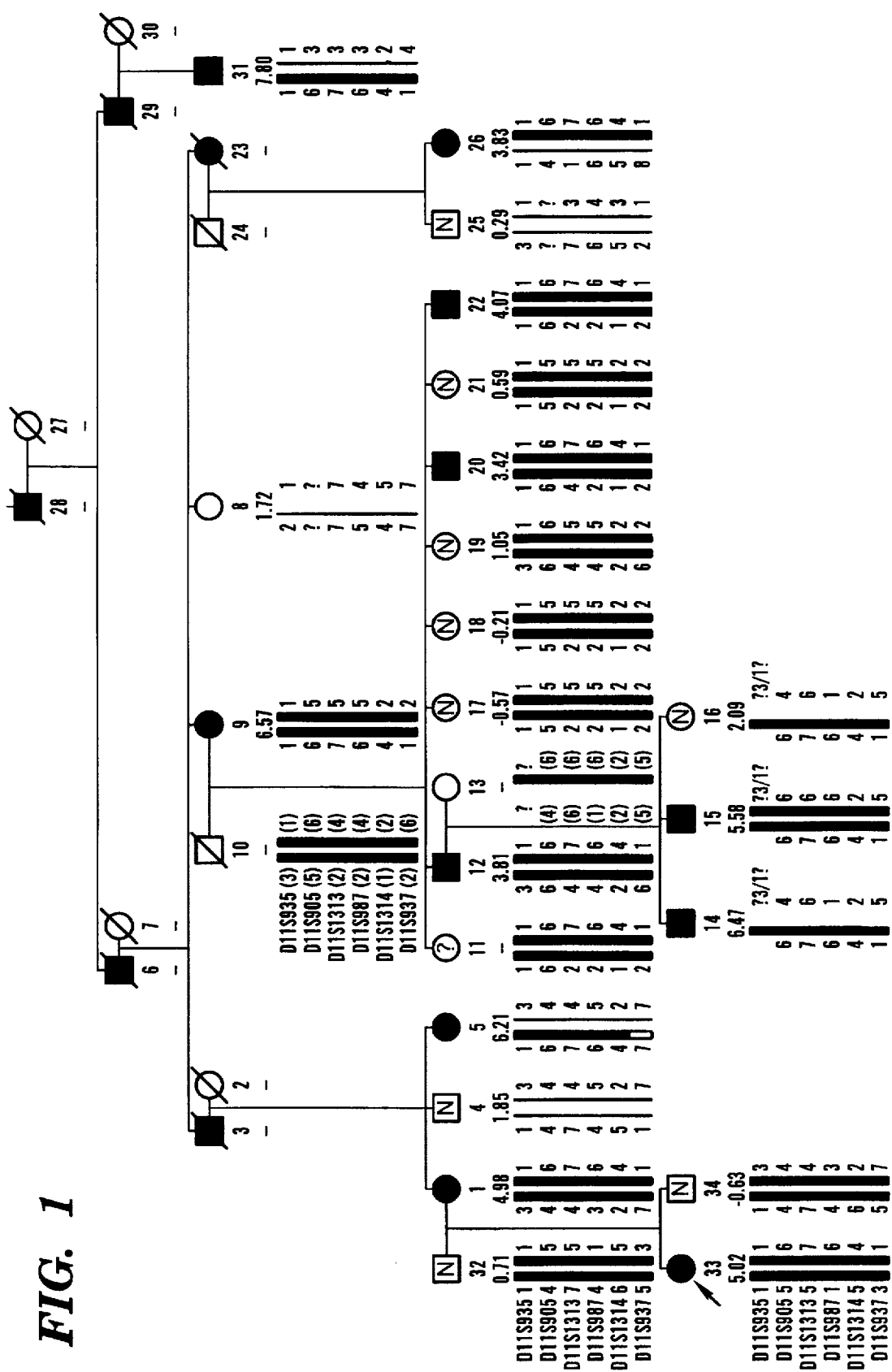
FIG. 1 shows the pedigree of the individuals used in the genetic linkage studies. Under each individual is an ID number, the z-score for spinal BMD, and the allele calls for the critical markers on chromosome 11. Solid symbols represent "affected" individuals. Symbols containing "N" are "unaffected" individuals. Symbols with question marks are of unknown phenotype. DNA from 22 individuals was genotyped, however, individual 11 was not included in the Linkage analysis because of incomplete phenotyping on her.

The present invention describes, for the first time, the location and chromosomal band which carries the gene responsible for high bone mass.

The present invention relates to the location of polymorphic markers on the long arm of human chromosome 11, which are linked to the autosomal dominant gene associated with high bone mass and enable linkage analysis to predict an affected individual having high bone mass. Linkage analysis with these polymorphisms can identify the inheritance of the high bone mass allele with 95% accuracy. Polymorphisms are DNA sequences located on the long arm of human chromosome 11. More specifically, these polymorphisms are in, or immediately adjacent to, the q12-13 bands on the long arm of human chromosome 11. The linkage analysis of the invention can be carried out by using any polymorphisms linked to the high bone mass allele. The use of the term polymorphism is intended to encompass any marker DNA sequence which is linked to the high bone mass gene. The polymorphism must be located close to, or be the same as, the high bone mass gene. If located close to the high bone mass gene, the polymorphism must be sufficiently close to the high bone mass gene such that the high bone mass gene and the marker are linked. Linkage may be determined by a sufficient LOD score or other acceptable statistical linkage determination.

The marker can be detected by a variety of methods. One method uses radioactive nucleotides in PCR amplification of the polymorphism, but other detection methods such as ligase chain reaction (LCR) can also be used. The polymorphism can be detectably labeled by a radioisotope or by chemical modification enabling direct detection of the polymorphism. Fluorescent or colorimetric means can also be used. Detection of the polymorphism can be indirect, e.g. a radioactive complementary strand of DNA, resulting from incorporation of radioactive nucleotides in a polymerase chain reaction. The polymorphism can also be detected by comparing the molecular weight of the protein (or peptide) encoded thereby to the molecular weight of the protein encoded by the wild-type DNA. Such detection involves gel electrophoresis and detecting of bands corresponding to particular molecular weights.

MATERIALS AND METHODS a. Phenotyping using DXA measurements

Spinal BMC and BMD measurements performed at Creighton University (Omaha, Nebr.) were made by DXA using a Norland Instruments densitometer (Norland XR2600 Densitometer, Dual Energy X-ray Absorptiometry, DXA). Spinal BMC and BMD at other locations used the machinery available. There are estimated to be 800 DXA machines currently operating in the U.S. Most larger cities have offices or imaging centers which have DXA capabilities, usually a Lunar or Hologic machine. These machines are coming into increasing use, and local operators are quite capable of providing information which is satisfactory for phenotyping the members of kindreds in this study. Each location that has provided spine BMC and BMD data has included copies of the printouts from their machines. This has allowed verification that the regions of interest for measurement of BMD have been chosen appropriately. In addition, complete clinical histories and skeletal radiographs were obtained.

The phenotype for this trait is defined by the following criteria: 1) very high spinal BMD; 2) a clinical history devoid of any known high bone mass syndrome; and 3) skeletal radiographs showing a normal shape of the appendicular skeleton.

b. Genotyping

Blood (20 ml) was drawn into lavender cap (EDTA containing) tubes by a certified phlebotomist. The blood was stored refrigerated until DNA extraction. DNA has been extracted from blood stored for up to 7 days in the refrigerator without reduction in the quality or quantity of yield. For those subjects that have blood drawn at distant sites (other physicians' offices, etc.), a shipping protocol was successfully used on more than a dozen occasions. Blood samples are shipped by overnight express in a styrofoam container with freezer packs to provide cooling. Lavender cap tubes are placed in individual plastic shipping tubes and then into "zip-lock" biohazard bags. When the samples arrive the next day, they are immediately processed to extract DNA.

The DNA extraction procedure used a kit purchased from Gentra Systems, Inc. (Minneapolis, Minn.). Briefly, the procedure involves adding 3 volumes of a RBC lysis buffer to the whole blood. After incubations for 10 minutes at room temperature the solution is centrifuged in a Beckman tabletop centrifuge at 2,000×g for 10 minutes. The white blood cell pellet was resuspended in Cell Lysis Buffer. Once the pellet was completely resuspended and free of cell clumps, the solution was digested with RNase A for 15 minutes at 37° C. Proteins were precipitated by addition of the provided Protein Precipitation Solution and removed by centrifugation. The DNA was precipitated out of the supernatant by addition of isopropanol. This method is simple and fast, requiring only 1-2 hours, and allows for the processing of dozens of samples simultaneously. The yield of DNA is routinely >40 μg/ml of whole blood and has a MW of >50 kb. DNA was archived by storing coded 50 μg aliquots at −80° C. as an ethanol precipitate.

DNA was genotyped using the fluorescence based marker sets (Reed et al. 1994) commercially available through Perkin Elmer Applied Biosystems (ABI PRISM™ Linkage Mapping Sets) using an Applied Biosystems automated DNA sequencing system (Model 377) running the GENES-CAN™ 672 and GENOTYPER™ software for allele identification and sizing. These marker sets have been developed for optimal use on this hardware/software by Perkin Elmer Applied Biosystems (Norwalk, Conn.) and are intended to be used in a multiplex format to facilitate rapid genotyping of large numbers of DNA samples. This linkage marker set contains 345 markers which cover the human genome (the X and Y chromosomes were excluded) at a spacing interval ranging from 7–22 cM. The spacing of these markers is such that less than 2% of the genome lies more than 10 cM from a marker and about 50% lies within 5 cM.

The PCR reactions were performed in one of two fashions. All reagents were purchased from Perkin Elmer—Applied Biosystems, Inc. ("PE-ABI") (Norwalk, Conn.). Initially, individual PCR reactions were performed with the markers from the Human Linkage Mapping Panels 12, 13, 15, 16, 17 and 18. Reactions were performed exactly as described by the supplier using AmpliTaq DNA Polymerase. The remaining Panels were performed in a multiplex fashion. Markers from each panel were multiplexed in the PCR reaction based on color (dye label). Thus, for each DNA sample only three reactions were performed with each panel (one blue, one green, and one yellow labeled group of markers). The multiplex PCR reactions were performed in a 50 μl reaction volume using the following final concentrations: 1X PCR Buffer II, 2.5 mM $MgCl_2$, 10 pmoles of each primer, 250 ng of DNA, and 3 units of AmpliTaq Gold DNA Polymerase. Thermal cycling was performed using a Perkin Elmer 9600 thermal cycler. Conditions were 95° C. for 5 minutes followed by 30 cycles of 95° C. for 1 minute, 60° C. for 1 minute, 72° C. for 1 minute; followed by a 30 minute extension at 60° C. After cycling, the reactions were cooled to 4° C. until removal from the thermal cycler. The three separate multiplex reactions were pooled at the following ratios: 5 μl each of the blue (Fam labeled) markers and green (Tet labeled) markers, 10 μl of the yellow (Hex labeled) markers and 20 μl of deionized water. Pooled reactions were stored at −20° C. until gel electrophoresis.

1.5 μl of pooled reactions were added to 3.5 μl of loading buffer containing deionized formamide, blue dextran and TAMRA 350 size standards (PE-ABI). After heating at 95° C. for 5 minutes to denature the DNA, the samples were loaded and electrophoresed exactly as described in the operator's manual for the Model 377 DNA Sequencer (PE-ABI, Foster City, Calif.).

After gel electrophoresis, the data was analyzed using GENESCAN™ and GENOTYPER™ software (PE-ABI). First, within the GENESCAN™ software the lane tracking was manually optimized prior to the first step of analysis. After the gel lane data was extracted, the standard curve profiles of each lane were examined and verified for linearity and size calling. Lanes which had problems with either of these parameters were re-tracked and verified. Once all lanes were tracked and the size standards were correctly identified, the data were imported into GENOTYPER™ for allele identification. To expedite allele calling (binning), the program Linkage Designer from the Internet web-site of Dr. Guy Van Camp (http://alt-www.uia.ac.be/u/dnalab/ld.html) was used. This program greatly facilitates the importing of data generated by GENOTYPER™ into the pedigree drawing program Cyrillic (Version 2.0, Cherwell Scientific Publishing Limited, Oxford, Great Britain) and subsequent linkage analysis using the program LINKAGE (Lathrop et al. 1985).

c. Linkage Analysis

Two-point and multipoint linkage analysis was performed using the MLINK and LINKMAP components of the program LINKAGE (Lathrop et al. 1985). Pedigree/marker data was exported from Cyrillic as a pre file into the Makeped program and converted into a suitable ped file for linkage analysis.

EXAMPLE I

The propositus was referred by her physicians to the Creighton Osteoporosis Center for evaluation of what appeared to be unusually dense bones. She was 18 years old and came to medical attention two years previous because of back pain which was precipitated by an auto accident in which the car in which she was riding as a passenger was struck from behind. Her only injury was soft tissue injury to her lower back that was manifested by pain and muscle tenderness. There was no evidence of fracture or subluxation on radiographs. The pain lasted for two years, although she was able to attend school full time. By the time she was seen in the Center, the pain was nearly resolved and she was back to her usual activities as a high school student. Physical exam revealed a normal healthy young woman standing 66 inches and weighing 128 pounds. Radiographs of the entire skeleton revealed dense looking bones with thick cortices. All bones of the skeleton were involved. Most importantly, the shapes of all the bones were entirely normal. The spinal bone mineral content (BMC) was 94.48 grams in L1-4, and the spinal bone mineral density (BMD) was 1.667 $gm/cm^2$ in L1-4. BMD was 5.62 standard deviations (SD) above peak skeletal mass for women. These were measured by DXA using a Hologic 2000$^+$. Her mother was then scanned and a lumbar spinal BMC of 58.05 grams and BMD of 1.500 $gm/cm^2$ were found. Her mother's values place her 4.12 SD above peak mass and 4.98 SD above her peers. Her mother was 51 years old, stood 65 inches and weighed 140 pounds. Her mother was in excellent health with no history of musculoskeletal or other symptoms. Her father's lumbar BMC was 75.33 grams and his BMD was 1.118 $gm/cm^2$. These values place him 0.25 SD above peak bone mass for males. He is in good health, is 72 inches tall and weighs 187 pounds.

These clinical data suggested that the propositus inherited a trait from her mother which resulted in very high bone mass, but an otherwise normal skeleton, and attention was focused on the maternal kindred.

Twenty two of these members have had measurement of bone mass by DXA. One case, the maternal grandfather of the propositus, is deceased, however, medical records, antemortem skeletal radiographs, and a gall bladder specimen embedded in paraffin for DNA genotyping were obtained. His radiographs show obvious extreme density of all of the bones available for examination including the femur and the spine, and he is included among the affected members. The pedigree of this kindred is shown in FIG. 1.

The portion of the kindred that was used for the whole genome screening and linkage analysis is shown in FIG. 1.

Twenty two known informative individuals were available for genotyping/phenotyping. One person (individual 11) is yet to be phenotyped by DXA and was excluded from the linkage analysis. To date, 192 members of the family have been ascertained. The pattern of inheritance of the high bone mass (HBM) trait in this family is that of an autosomal dominant trait. X-linkage is ruled out by the presence of male to male transmission from individual 12 to 14 and 15.

Table 1 summarizes the DXA determined spinal BMD on the twenty-one individuals analyzed by linkage analysis. It was decided initially to use the operational definition of an age and sex adjusted z-score greater than 3.0 as representing affected individuals. None of the z-scores overlap between affected and unaffected individuals. Unaffected individuals have a mean spinal BMD and distribution which is distinguishable from a random sample of the population.

Based upon the bimodal distribution of z-scores in Table 1, the linkage analysis was performed using an autosomal dominant, full penetrance model in the first attempt to identify linked markers.

The genome screening was performed using the 345 markers contained within the autosomal PE-Applied Biosystems Linkage Mapping Panels. The success rate of first use of these markers is shown in Table 2. Little difference was found between individual or multiplex PCR in terms of the percentage of markers that yielded complete allele information on the first attempt versus the percentage that had to be repeated. The advantage of the multiplex PCR is the speed with which the panel sets can be analyzed. It is estimated that multiplexing represents a 10 fold increase in throughput.

The only region of linkage observed was to markers found on chromosome 11. The values for $\hat{\theta}$ and $Z_{max}$ are shown in Table 3. As stated above, an autosomal dominant, full penetrance model was used for the initial two-point linkage analysis. Once linked markers were found, the haplotypes of the genotyped kindred members were examined and it was determined that one person (individual 16) carried the affected haplotype but was called unaffected based on her spinal BMD. Her phenotype is being re-evaluated, but this raised a concern about the correctness of the model. Therefore, linkage analysis was then performed using an autosomal dominant, partially penetrant (0.9) trait. This improved the values for $\hat{\theta}$ and $Z_{max}$ as shown in Table 3. Given that bone density is really a continuous trait, a third model using a quantitative trait with individual spinal BMD z-scores was also used. As shown in Table 3, the values $\hat{\theta}$ and $Z_{max}$ are highest with this model.

Figure 2:
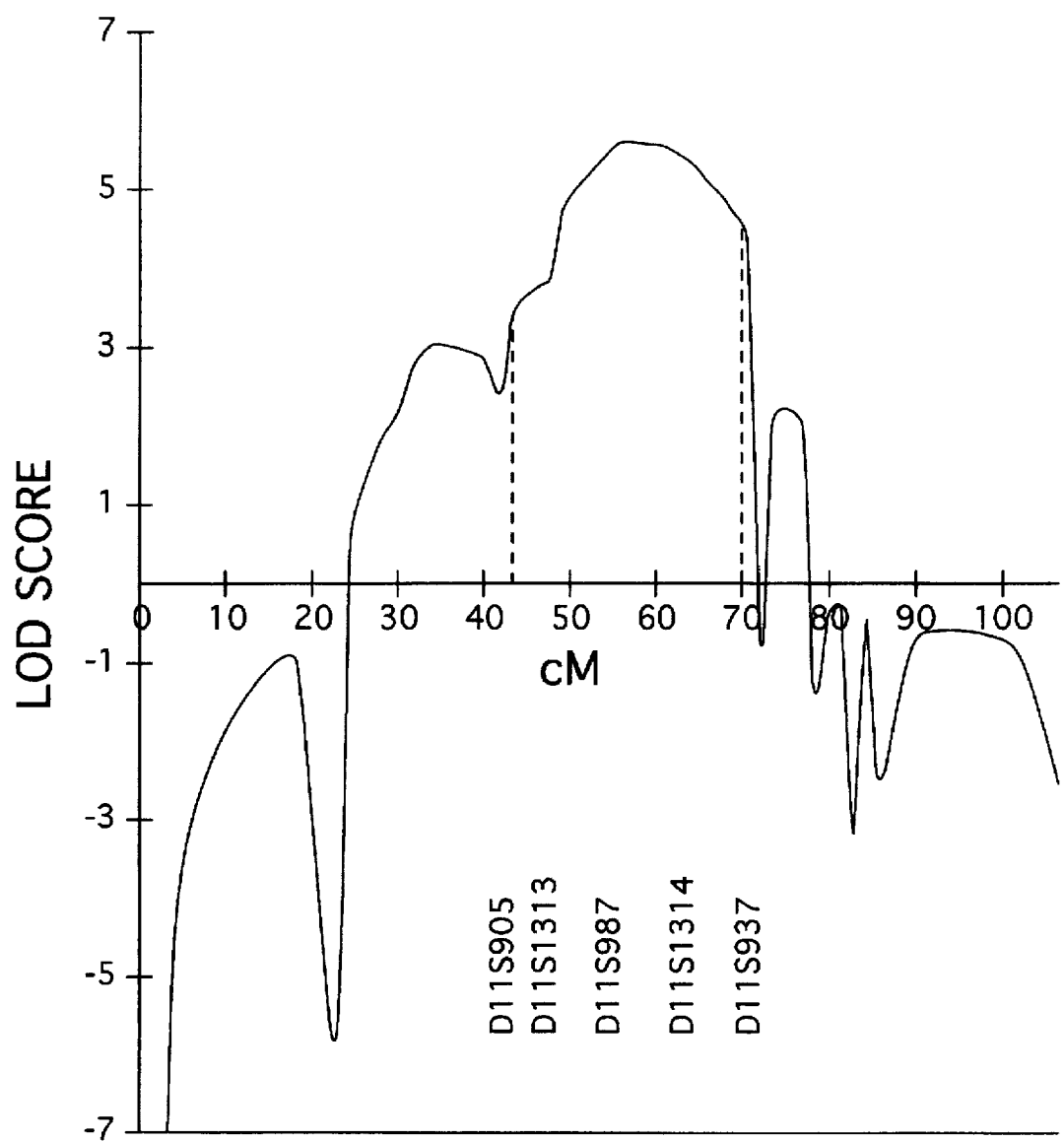
FIG. 2 shows the multipoint map of chromosome 11. Marker D11S987 gave the highest LOD score (5.74). The 95% confidence interval for the probable location of the Hbm gene is shown by the dashed lines and is bounded by markers D11S905 and D11S937.

A multipoint analysis was then performed on selected markers from chromosome 11 using the quantitative trait model. The multipoint map is shown in FIG. 2. The maximum LOD score (5.74) was found near marker D11S987 (map position 55 in FIG. 2) and the 95% confidence interval places the gene for the HBM trait between D11S905 and D11S937, a region of about 30 cM (map position 41 to 71 in FIG. 2). Haplotype analysis also places the Hbm gene in this same region. Further descriptions of the markers D11S987, D11S905, and D11S937 can be found in Gyapay et al. 1994.

Thus, the Hbm locus was mapped to chromosome 11q12-13 by analyzing DNA for linked markers from 22 members of a large, extended kindred. A highly automated technology was used with a panel of 345 fluorescent markers which spanned the 22 autosomes at a spacing interval ranging from 6-22 cM. Only markers from this region of chromosome 11 showed evidence of linkage (LOD score >3.0). The highest LOD score obtained by two-point and multipoint analysis was D11S987. The 95% confidence interval places the Hbm locus between markers D11S905 and D11S937.

At present, there are no clearly obvious mapped genes in this region that could account for the Hbm trait, although several genes have been mapped in this region. One locus of interest is the locus for osteoporosis pseudoglioma syndrome (OPS) (Gong et al. 1996) which also maps to the same interval. This is an autosomal recessive trait of raging juvenile osteoporosis and other complications. This is the opposite phenotype of the trait described herein.

The kindred described has several features of great interest, the most important being that their bones, while very dense, have absolutely normal shape. The outer dimensions of the skeletons of the affected individuals are normal. Medullary cavities are present, though reduced in size, and there is no interference with hematopoiesis. The affected members seem to be resistant to fracture. There are no neurologic symptoms, and no symptoms of impairment of any organ or system function in the members examined. Affected members of the kindred live to advanced age without undue illness or disability. Furthermore, this phenotype matches no other disorders of bone such as progressive diaphyseal dysplasia, pycnodystosis, or melorheostosis.

Clearly, the Hbm locus in this family has a very powerful and substantial role in regulating bone density, and its identification could be an important step in understanding the pathway(s) that regulate bone density and the pathogenesis of diseases such as osteoporosis.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

The mean, standard deviation and range of spinal BMD, age and sex adjusted z-scores for the "affected" and "unaffected" individuals in FIG. 1.

| UNAFFECTED (n = 11) | |
|---|---|
| mean ± sd. | 0.44 ± 0.92 |
| range | −1.07 – 2.09 |
| AFFECTED (n = 11) | |
| mean ± sd. | 5.22 ± 1.48 |
| range | 3.81 – 7.80 |

TABLE 2

First attempt success rates for markers analyzed in individual PCR reactions versus multiplex PCR reactions of 3–6 primers.

| Individual PCR | |
|---|---|
| # of markers | 78 |
| lo success rate | 93% (73/79) |
| Multiplex PCR | |
| # of markers | 267 |
| lo success rate | 92% (245/267) |

TABLE 3

LOD scores obtained for markers linked to the Hbm locus on chromsome 11 under three models. Bone density is a quantitative trait. However, given the bimodal distribution of z-scores shown in Table 1, we also modeled the inheritance of the Hbm trait as an autosomal dominant with either full (b) or partial (c) penetrance. For these two models, we classified all persons with a z-score above 3.0 as "affected".

| Model | Marker | θ | $Z_{max}$ |
|---|---|---|---|
| a. Quantitative Trait | D11S905 | 0.051 | 2.096 |
|  | D11S1313 | 0.000 | 2.679 |
|  | D11S987 | 0.000 | 5.207 |
|  | D11S1314 | 0.000 | 3.963 |
|  | D11S937 | 0.061 | 2.747 |
| b. Affectation with Full Penetrance | D11S905 | 0.064 | 2.089 |
|  | D11S1313 | 0.107 | 1.572 |
|  | D11S987 | 0.044 | 4.055 |
|  | D11S1314 | 0.000 | 2.961 |
|  | D11S937 | 0.123 | 1.974 |
| c. Affectation with Partial Penetrance (Penetrance = 0.9) | D11S905 | 0.000 | 2.454 |
|  | D11S1313 | 0.000 | 1.932 |
|  | D11S987 | 0.000 | 4.474 |
|  | D11S1314 | 0.000 | 3.172 |
|  | D11S937 | 0.089 | 2.136 |

REFERENCES

Black, L. J., et al., J Clin Invest 93:63–69 (1994).
Botstein, D. R. L., et al., Am J Hum Genet 32:314–331 (1980).
Eisman, J. A., J Bone Miner Res 10:1289–1293 (1995).
Garnero, P., et al., J Bone Miner Res 10:1283–1288 (1995).
Gong, G., et al., J Bone Miner Res 10:S462 (1995) [Abstract].
Gong, Y., et al., Am J Hum Genet 59:146–151 (1996).
Gyapay, G., et al., Nature Genetics, Vol. 7 (entire volume) (1994).
Hosoi, T., et al., J Bone Miner Res 10:S170 (1995) [Abstract].
Howard, G., et al., J Clin Endocrinol Metab 80:2800–2805 (1995).
Hui, S. L., et al., Ann Int Med 111:355–361 (1989).
Hui, S. L., et al., Osteoporosis Int 1:30–34 (1995).
Johnson, M. L., et al., J Bone Miner Res 10:S367 (1995) [Abstract].
Kelly, P. J., et al., J Bone Miner Res 8:11–17 (1993).
Krall, E. A. and Dawson-Hughes, B., J Bone Miner Res 8:1–9 (1993).
Lathrop, G. M., et al., Am J Hum Genet 37:482–498 (1985).
Lathrop, G. M., et al., Proc Natl Acad Sci USA 81:3443–3446 (1984).
Love, R. R., et al., N Engl J Med 326:852–856 (1992).
Morrison, N. A., et al., Nature 367:284–287 (1994).
Morrison, N. A., et al., J Bone Miner Res 10:S170 (1995) [Abstract].
Morton, N. E., Prog Clin Biol Res 147:245–265 (1984).
Morton, N. E., et al., Am J Hum Genet 38:868–883 (1986).
Ott, J., Am J Hum Genet 28:528–529 (1976).
Overgaard, K., et al., Br Med J 305:556–561 (1992).
Peacock, M., J Bone Miner Res 10:1294–1297 (1995).
Pocock, N. A., et al., J Clin Invest 80:706–710 (1987).
Reed, P. W., et al., Nature Genetics 7:390–395 (1994).
Slemenda, C. W., et al., J Bone Miner Res 6:561–567 (1991).
Young, D., et al., J Bone Miner Res 10:558–567 (1995).

What is claimed is:

1. A method for detecting the presence in a subject of a polymorphism linked to an autosomal dominant gene associated with high bone mass which comprises:

analyzing human chromosome 11 of the subject and detecting the presence of a polymorphism located about 30 cM around D11S987 and linked to the autosomal dominant gene associated with high bone mass, wherein the presence of the polymorphism is indicative of a subject having high bone mass.

2. The method of claim 1 wherein the polymorphism is located on the q12-13 band of the long arm of human chromosome 11.

3. The method of claim 1 wherein the polymorphism is located between D11S905 and D11S937, inclusive.

4. The method of claim 1 wherein the polymorphism is selected from the group consisting of D11S987, D11S905, and D11S937.

5. The method of claim 1 wherein the polymorphism is located about 15 cM around D11S905.

6. The method of claim 5 wherein the polymorphism is D11S905.

7. The method of claim 1 wherein the polymorphism is located about 15 cM around D11S937.

8. The method of claim 7 wherein the polymorphism is D11S937.

9. The method of claim 1, wherein the polymorphism is D11S987.

10. The method of claim 1 wherein the analyzing is carried out by:

amplifying the polymorphism;

separating the amplified polymorphism to generate a polymorphism pattern; and correlating the presence or absence of the polymorphism with the respective presence or absence of the autosomal dominant gene associated with high bone mass by comparing a corresponding polymorphism pattern for family members showing segregation between the autosomal dominant gene and the polymorphism.

* * * * *